United States Patent [19]

Okada et al.

[11] Patent Number: 5,905,035
[45] Date of Patent: May 18, 1999

[54] FUNGUS USEFUL FOR CHITIN PRODUCTION

[75] Inventors: Takashi Okada, Hartsdale, N.Y.; Isao Kubo, Moraga, Calif.

[73] Assignee: Asahi Kasei Kogyo Kabushiki Kaisha, Osaka, Japan

[21] Appl. No.: 08/839,607

[22] Filed: Apr. 15, 1997

[51] Int. Cl.⁶ .............................. C12P 1/02; C12P 19/04; C12N 1/14
[52] U.S. Cl. ...................... 435/254.1; 435/101; 435/171; 514/55
[58] Field of Search .................................. 435/101, 171, 435/254.1; 514/55

[56] References Cited

U.S. PATENT DOCUMENTS 3,903,268  9/1975  Balassa ..................................... 514/55
5,232,842  8/1993  Park et al. .............................. 435/101

*Primary Examiner*—Leon B. Lankford, Jr.
*Assistant Examiner*—Christopher R. Tate
*Attorney, Agent, or Firm*—Pennie & Edmonds LLP

[57] ABSTRACT

The present invention relates to *Mucoriopsis ellipsoidus* fungus. The invention also provides methods of extracting chitin from *Mucoriopsis ellipsoidus* and the chitin produced by this process.

1 Claim, 11 Drawing Sheets

FUNGUS USEFUL FOR CHITIN PRODUCTION

1. FIELD OF THE INVENTION

The present invention relates to *Mucoriopsis ellipsoidus* fungus. The invention also provides methods of extracting chitin from *Mucoriopsis ellipsoidus* and the chitin produced by this process.

2. BACKGROUND OF THE INVENTION

Chitin is the second most abundant natural biopolymer in the world, next only to cellulose, and the most abundant naturally occurring polysaccharide that contains amino sugars. Chitin is found as a component of crustacean shells, insect exoskeletons, fungal cell walls, microfauna, and plankton. The various sources of chitin differ somewhat in their structure and percent chitin content. Chitin naturally occurs in association with proteins and minerals such as calcium carbonate.

Chitin is a polymer formed primarily of repeating units of beta(1–4) 2-acetamido-2-deoxy-D-glucose (or N-acetylglucosamine or GlcNAc). Approximately 16% of the naturally occurring chitin polysaccharide units are deacetylated.

Most commercial applications involving chitin make use of its deacetylated derivative, called chitosan. Chitosan is a polysaccharide formed primarily of repeating units of beta (1–4) 2-amino-2-deoxy-D-glucose (or D-glucosamine). Unlike most polysaccharides, chitosan has a positive charge. This charge is the result of the amino groups contained in chitosan taking on hydrogen ions at low pH. Generally, about 80% of the chitosan polysaccharide units are deacetylated and 20% remain acetylated. These values vary according to the chitin sources and methods by which the polysaccharide is processed. Chitosan is produced by hydrolyzing the N-acetyl linkage in chitin with concentrated alkali and then rinsing away the alkali by slurrying the material with water.

The vast commercial potential for applications using chitin and chitosan biopolymers has only recently been realized. Commercial uses for chitin and chitosan include pharmaceuticals and other aspects of health care such as wound care products, and medical implants, as well as applications in agriculture, cosmetics, food additives and separations, textiles, and water and waste water treatment.

Applications which take advantage of the biocompatibility and bioactivity of chitin and chitosan exemplify the numerous useful applications of these biopolymers. For example, by inhibiting the formation of fibrin strands in wounds, chitosan inhibits the formation of scar tissue. Because of this property, chitosan, along with chitin, can be used to form sutures, dressings, and other healing agents with properties not found in competing products. Additionally, since lysozyme present in wounds breaks down chitin, sutures and wound dressing can be made that will break down instead of needing to be removed. The bioactivity properties of chitin and chitosan is also important in nonmedical applications. For example, chitin stimulates soil microorganisms to produce enzymes that break down chitin. These enzymes attack pesticidal organisms such as soil nematodes that contain chitin as part of their structure. Additionally, chitin has been found to stimulate the growth of bacteria in the gut, a property that could have application for food, feed and cell culture.

Chitin also has potential applications in the textile industry. Recently, a novel chitin fabric called "Biochitin" has been developed. Biochitin, is a highly breathable fabric consisting of chemically treated chitin applied to a porous polyurethane resin coated on a nylon sheet. The chitin layer serves to absorb perspiration, and has over twice the water-absorbing capacity of conventional materials.

The current commercial source of chitin and chitosan is shellfish waste. Fungi also provide a potential major source of chitin which can be derived from fermentation wastes or grown specifically for chitin/chitosan manufacture. Methods have been developed for extracting chitin from fungus, although this process has not been implemented on a commercial scale.

Extraction of chitin from fungi provides a more controllable route to get a purer and more consistent chitin than obtained from shellfish waste. Furthermore, chitin extracted from fungi is less likely to include allergenic contaminants than seafood derived chitin and is therefore more suitable for use in textile, food and pharmaceutical applications. There is therefore a great need for identifying fungal sources which produce quantities of chitin sufficient to justify commercial scale up, and to harvest the chitin produced by these fungal sources.

There are presently twenty-two described genera in the Mucoraceae family. Members of this family are characterized as follows;

reproduction asexually by aplanospores (nonmotile sporangiospores), asexual spores are not conidia; saprobic, not mycorrhiza, many spored sporangia present, sporangial wall not splitting into 2 halves, sporangia globose, sporangia wall thin, sporangia with a distinct columella, without sporangiola (Ainsworth, G. C., F. K. Spparow, A. S. Sussman, 1973, "The Fungi, An Advanced Treatise. Volume 4B, A Taxonomic Review with Keys: Basidiomycetes and Lower Fungi", Academic Press, Inc. London).

3. SUMMARY OF THE INVENTION

The present invention provides for a substantially pure *Mucoriopsis ellipsoidus* strain as deposited with the ATCC and assigned accession number ATCC 74375.

The invention further provides methods of extracting chitin comprising isolating a sample of *Mucoriopsis ellipsoidus* and extracting the sample with both an alkali to remove protein and a solution to remove the lipid contents of this sample.

The invention also provides a method of extracting chitin, comprising isolating a sample of *Mucoriopsis ellipsoidus* and extracting the sample with 5% NaOH. This NaOH treated sample is then centrifuged at 15400×G for 15 minutes and the resulting pellet is neutralized. The neutralized pellet is extracted with an equal volume of methanol and the methanol treated sample is centrifuged at 15400×G for 15 minutes. The resulting pellet is collected.

The invention further provides for the chitin product extracted according to these methods.

The present invention may be understood more fully by reference to the following figures, detailed description and illustrative examples which are intended to exemplify non-limiting embodiments of the invention.

4. BRIEF DESCRIPTION OF THE FIGURES

FIG. 1. *Mucoriopsis ellipsoidus*. Diagrammatic representation of *Mucoriopsis ellipsoidus* : (A), stolon and rhizoid; (B), sporangiophore and sporangia; (C), columella; and (D), sporangiospore.

FIG. 10. NMR analysis of commercially obtained chitin (FIG. 10(*a*)) and chitosan (FIG. 10(*b*)). NMR analysis of the sample resulting after the *Mucoriopsis ellipsoidus* alkali treatment precipitate is subjected to a lipid extraction treatment and vacuum dried according to the methods detailed in Section 5.3 (FIG. 10(*c*)).

5. DETAILED DESCRIPTION OF THE INVENTION

Presented below, are a description of the *Mucoriopsis ellipsoidus* fungus, methods for growing Mucoriopsis, *ellipsoidus,* methods for extracting chitin from *Mucoriopsis ellipsoidus* and the chitin and/or chitin derivatives extracted by this process.

5.1 Mucoriopsis *ellipsoidus*

*Mucoriopsis ellipsoidus* grows rapidly on MEA media at 25° C. and in one day attains a radial growth of 25 mm in diameter and a height of over 4(–5) mm. After a period of two days of growth, *Mucoriopsis ellipsoidus* covers the whole plate (93 mm).

In the following description, the scales of color are based on the book, Kornerup, A. and J. H. Wanscher: *Methuen Handbook of Color* of Eyre Methuen Ltd., London, 1983, 252pp. The *Mucoriopsis ellipsoidus* colony has a light yellow center (4A3-4), with mature sporangia having a yellow-white margin (4A4). Both odor and exudate are lacking from the *Mucoriopsis ellipsoidus* colony. The color of the colonies observed from the bottom of Petri dish is light yellow (4A4). Both stolons and rhizoids are present and branched. The stolons of *Mucoriopsis ellipsoidus* are up to 13 μm wide, have a smooth to roughened wall, and are yellowish-grey (4B2). Septate sporangiophores randomly arise from the stolons and are not opposite to the rhizoids touching the substrate. The sporangiophores are variable in length, and range up to 4 mm in height and 10 μm in width. The *Mucoriopsis ellipsoidus* sporangiophores are golden-grey in color (4C2). The sporangiophores, are mostly simple and are rarely branched once. The wall of the sporangiophore is smooth to roughened, nonapophysate and slightly attenuated towards the apex. The sporangia columellate is globose, ranging in diameter from 27–30 μm, and is grayish-yellow in color (4C9). The sporangia columellate of *Mucoriopsis ellipsoidus* are very finely roughened, deliquescent at maturity, and have an indistinct collar. The columella is globose to subglobose, ranging in diameter from 11.1–19.0 μm and has a smooth hyaline. The *Mucoriopsis ellipsoidus* sporangiospore is oval to ellipsoidal and rarely subglobose in shape. The sporangiospore has a smooth hyaline, is thin-walled, and ranges in size from 4–8×1.5–4 μm. It is not known whether *Mucoriopsis ellipsoidus* has zygospores. Chlamydospores are absent from *Mucoriopsis ellipsoidus.*

Optimum growth of *Mucoriopsis ellipsoidus* was observed at 25° C. No growth was observed at temperatures of 5° C. or 40° C. The observed growth under these temperature regimes indicate that *Mucoriopsis ellipsoidus* is nonthermophilic.

Because *Mucoriopsis ellipsoidus* reproduces asexually by aplanospores (nonmotile sporangiospores), it belongs to the Zygomycetes. Because asexual spores of *Mucoriopsis ellipsoidus* are not conidia, saprobic, *Mucoriopsis ellipsoidus* belongs to the Mucorales. And the characteristics such as, not mycorrhiza, many spored sporangia present, sporangial wall not splitting into 2 halves, sporangia globose, sporangia wall thin, sporangia with a distinct columella and without sporangiola, indicate that *Mucoriopsis ellipsoidus* belongs to the Mucoraceae.

Of the twenty two described genera in the Mucoraceae, *Mucoriopsis ellipsoidus* showed similarity in aspects to Mucor, Actinomucor, and Rhizomucor. Barron, G. L., 1980, Can. J. Bot. 58:2450–2453; Benjamin, C. R., and C. W. Hesseltine, 1957, Mycologia 49:240–249; Hesseltine, C. W. and J. J. Ellis, 1973, Mucorales in the Fungi, An Advanced Treatise (G. C. Ainsworth, F. K. Sparrow, and A. S. Sussman eds.) pp. 187–217; Schipper, M. A., 1978, Stud. Mycol. 17:1–52; Schipper, M. A., 1978, Stud. Mycol. 17:53–71; Schipper, M. A., 1986, Mycotaxan 27:83–86; Schipper, M. A., and R. A. Samson, 1994, Mycotaxan 50:475–491. *Mucoriopsis ellipsoidus* is distinguished from Mucor in having a well-developed rhizoid. Unlike Actinomucor, *Mucoriopsis ellipsoidus* lacks branched, racemose sporangiophores, which bear a terminal sporangium and subterminal often subtended by whorls of smaller sporangia. The light yellow or yellowish-white color of *Mucoriopsis ellipsoidus* and the absence of growth at 40° C. distinguish *Mucoriopsis ellipsoidus* from Rhizomucor.

Therefore, we concluded that *Mucoriopsis ellipsoidus* belongs to novel genera in the Mucoraceae.

A culture of *Mucoriopsis ellipsoidus* was deposited on July 16, 1996, with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned accession number ATCC 74375.

5.2 Methods for Growing *Mucoriopsis ellipsoidus*

Mucoriopsis cultures are initiated, by inoculating nutrient medium with *Mucoriopsis ellipsoidus* cells under sterile conditions. The nutrient medium must be free of all other microorganisms, therefor all materials including water, organic compounds, and inorganic components used in the preparation of the nutrient media must be sterile. In addition, all procedures involved in this operation must be conducted under strictly sterile conditions, i.e., all containers, all transfers of substances from one vessel to another, etc. must be performed in a sterile environment.

Listed below are formulas which may be followed in preparing media for culturing *Mucoriopsis ellipsoidus*. It is to be understood that while such media is to be used as a guide, it is intended that routine variations or substitutions of such media which contribute to a media capable of sustaining Mucoriopsis growth sufficient for the chitin preparative processes described herein are also within the scope of the present invention.

MEA medium

Malt extract 20 g, Glucose 20 g, Peptone 1 g, Agar 20 g, Distilled water 1 L

Yeast-Malt extract agar

Yeast extract 0.3%, Malt extract 0.3%, Dextrose 0.5%, Agar 2%

Yeast-Malt extract broth

Yeast Extract 1%, Malt extract 1%, Dextrose 2%

5.3 Processes for Isolating Chitin from *Mucoriopsis ellipsoidus*

Presented in this Section are methods which may be utilized for the preparation of chitin from *Mucoriopsis ellipsoidus* grown on media such as that described, above, in Section 5.2.

Chitin may be extracted from the fungal cell bodies by subjecting the contents of the *Mucoriopsis ellipsoidus* sample to chemical treatment. To minimize contamination of the chitin end product, the sample is subjected to a series of extractions, each designed to remove impurities having different properties. These extractions may include, but are not limited to, an alkali extraction, a lipid extraction, and a hot water treatment.

Alkali extraction involves treating the samples with a solution of sufficiently high pH so as to degrade and solubilize the protein content of the sample. According to this method, the alkali treated sample is centrifuged at 15400×G for 15 minutes and the pellet neutralized and retained for chitin isolation. In a preferred embodiment the alkali treatment is performed with NaOH. In a more preferred embodiment, the alkali extraction is performed in a solution having a final concentration of 2.5% to 10% NaOH. In a most preferred embodiment, the final concentration of the alkali extraction solution is 5% NaOH. The temperature and time parameters of the alkali extraction will differ according to the concentration of the alkali used in the extraction and may be routinely optimized. Routine modifications of the alkali extraction technique described herein are within the scope of the invention. Additionally, while the method and chemicals for alkali extraction described herein are preferred, other methods routinely used to extract protein from a sample, such as treatment with proteinase K, are also within the scope of the invention.

Lipid extraction may be performed on the *Mucoriopsis ellipsoidus* sample with organic solvents or other solutions routinely used for such a purpose, such as, detergents. According to this method, the solution containing the solubilized lipid is separated from chitin using routine techniques such as centrifugation. In one embodiment, lipid containing solution is separated from chitin by centrifuging the sample at 15400×G for 15 minutes and discarding the supernatant. Other methods and compositions for lipid extraction may be routinely applied and are included within the scope of this invention. In a preferred embodiment, lipid extraction is performed with an organic solvent. In a most preferred embodiment, lipid extraction is performed with methanol.

Hot water extraction may also be performed on the *Mucoriopsis ellipsoidus* sample to remove contaminants that are soluble in water at elevated temperatures. According to this method, the insoluble contaminant is separated from the chitin containing solution using techniques such as phase separation or centrifugation. In one embodiment, the heat treated sample is centrifuged at 15400×G for 15 minutes and the supernatant is retained for chitin isolation. In a preferred embodiment, the treatment occurs at water temperatures of 50° C. to 65° C. In a most preferred embodiment, hot water treatment occurs at 60° C.

In one embodiment, *Mucoriopsis ellipsoidus* sample is subjected to both the protein extraction and lipid extraction methods discussed supra. In a preferred embodiment, the *Mucoriopsis ellipsoidus* sample is subjected to the protein extraction, lipid extraction, and hot water treatment. In another preferred embodiment, the *Mucoriopsis ellipsoidus* sample is subjected first to the protein extraction; second, to the lipid extraction; and third, to the hot water treatment described supra.

The chitin preparation resulting from any of the foregoing procedures or combinations thereof can be further purified using techniques well known in the art.

Additionally, the chitin preparations isolated according to the methods described herein can be further characterized using techniques well known in the art, including but not limited to circular dichroism, X-ray diffraction, infra-red and NMR spectral analyses.

5.4 Process for Derivatizing Chitin from *Mucoriopsis ellipsoidus*

The chitin isolated according to methods of Section 5.3 may be derivatized, using a variety of controlled conditions and procedures known in the art. Such derivatized compounds may include but are not limited to, partially or completely deacetylated chitin which has been modified via chemical and/or enzymatic means (e.g. 50% NaOH, 100 C°, 3hr). Additionally, chitin or its deacetylated derivative, may be derivatized by being sulfated, phosphorylated, and/or nitrated. The deacetylated chitin of the invention may also be used to prepare a variety of organic salts and/or metal chelates. Further, the chitin or a derivative thereof of the invention may be either covalently or noncovalently attached to any of a variety of molecules. Still further, techniques well known in the art may be applied to subject the chitin of the invention, or a derivative thereof, to controlled hydrolysis conditions which yield groups of molecules having discrete molecular weight and/or chemical or biological properties.

The chitin of the invention may be deacetylated by treatment with a base to yield glucosamines with free amino groups. This hydrolysis process may be carried out with solutions including but not limited to concentrated sodium hydroxide or potassium hydroxide at elevated temperatures. To precisely control the extent of deacetylation and to avoid degradation of the main carbohydrate chain of the polysaccharide molecule, an optional procedure involves use of the enzyme chitin deacetylase. Such a deacetylase enzymatic procedure is well known to those of skill in the art and may be performed as in U.S. Pat. No. 5,219,749, which is incorporated herein, by reference in its entirety.

6. EXAMPLE

Extraction of Chitin from *Mucoriopsis ellipsoidus*

6.1 Materials and Methods

Alkali and Lipid Extraction. The fungal species *Mucoriopsis ellipsoidus* was grown on MEA (defined above) media at 25° C. and the cells harvested. Sodium hydroxide was added to the sample, to a final concentration of 5% and this solution was incubated with gentle agitation at 80° C. for 30 minutes. The solution was then centrifuged at 15400×G for 15 minutes. The pellet was resuspended in water and combined with an equal volume of methanol. This mixture was incubated at room temperature for 2 hours, with gentle agitation and then centrifuged at 15400×G for 15 minutes. The precipitate was then vacuum dried. The product was characterized by infra-red and $^{13}$C-Cross-polarization/ magnetic angle spinning nuclear magnetic resonance spectral analyses. See FIGS. 5 and 10, respectively.

Figure 6:
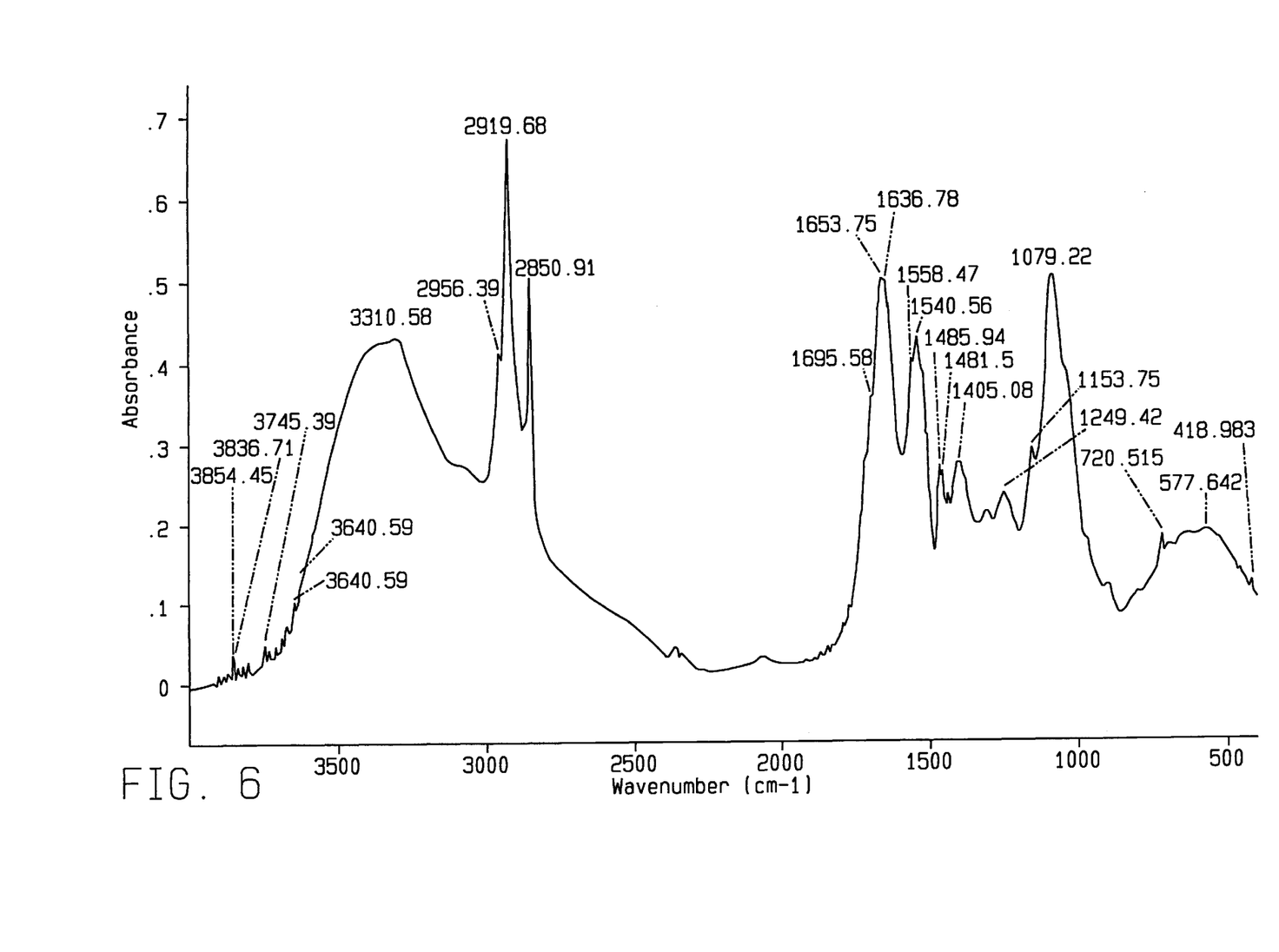
FIG. 6. Infra-red spectra analysis of the sample resulting after the *Mucoriopsis ellipsoidus* alkali treatment supernatant is subjected to a lipid extraction treatment and vacuum dried according to the methods detailed in Section 5.3.

The supernatant of the alkali extraction treatment was neutralized to a pH of around 7 by the addition of HCl. This neutralized solution was then centrifuged at 15400×G for 15 minutes and the pellet resuspended in water and combined with an equal volume of methanol. This mixture was incubated at room temperature for 2 hours, with gentle agitation and centrifuged at 15400×G for 15 minutes. The pellet was then vacuum dried. The product was characterized by infra-red spectral analysis. FIG. 6.

Figure 7:
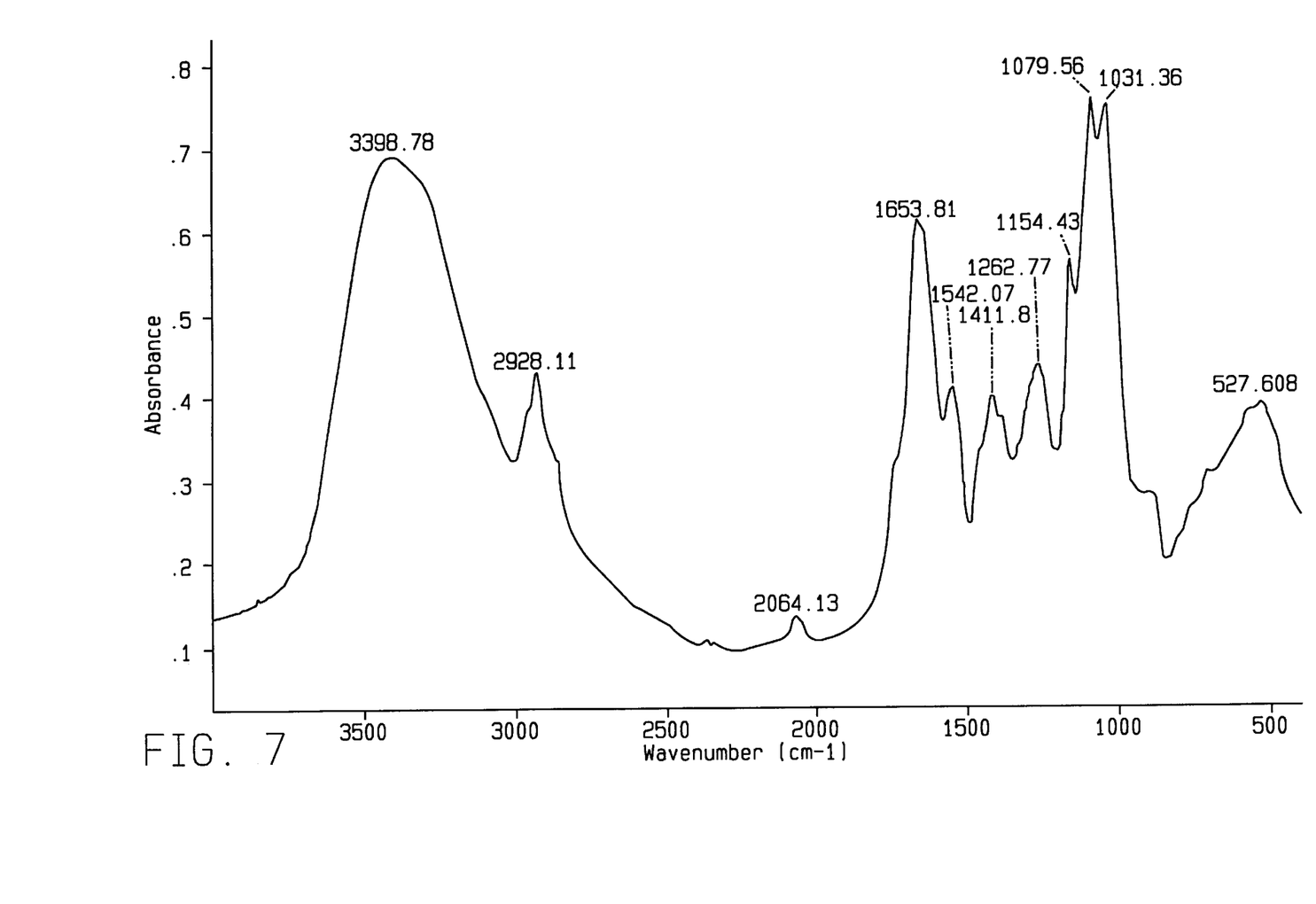
FIG. 7. Infra-red spectra analysis of the sample resulting after the *Mucoriopsis ellipsoidus* sample is subjected to a lipid extraction treatment and the precipitate is vacuum dried according to the methods detailed in Section 5.3.
Figure 8:
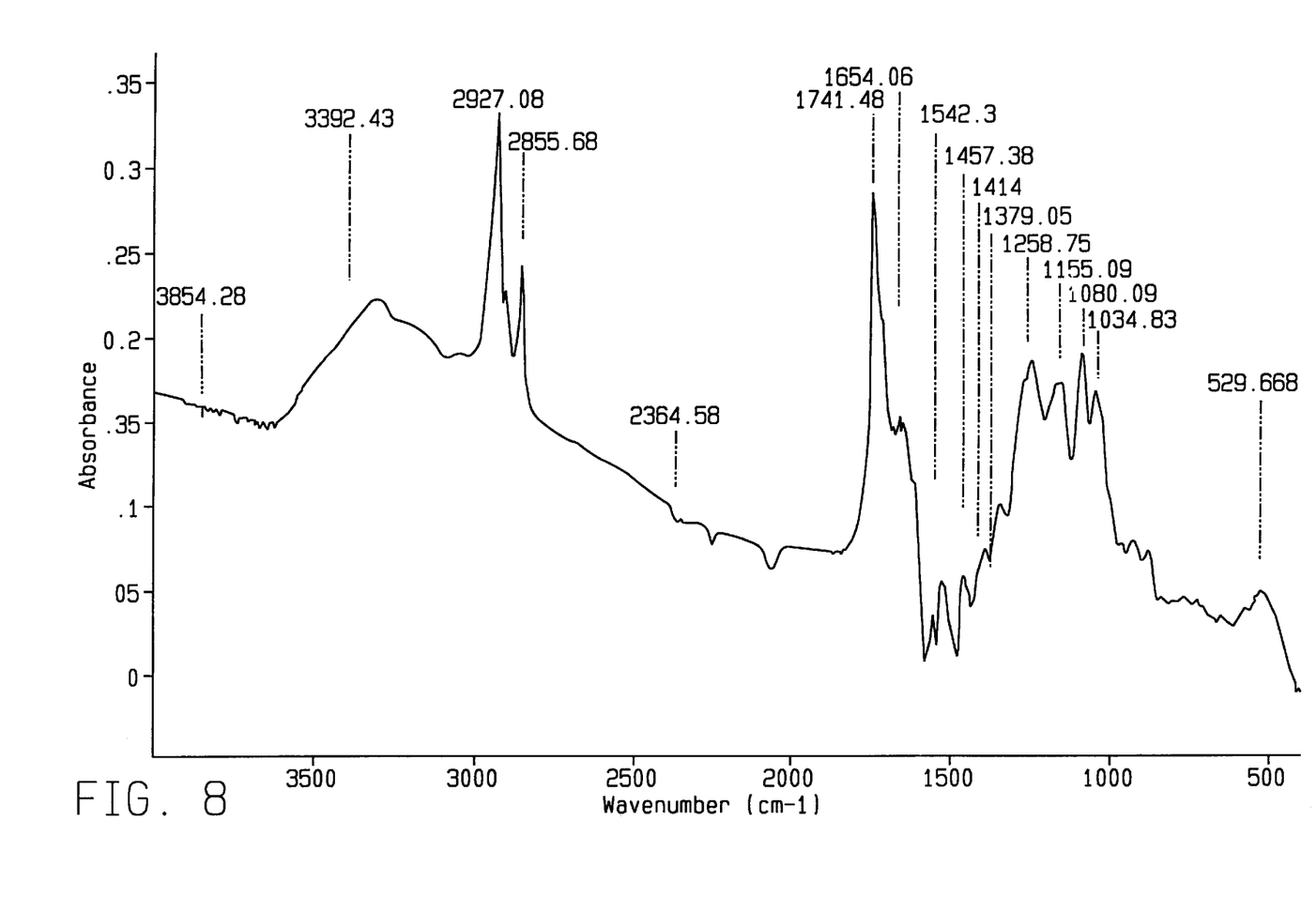
FIG. 8. Infra-red spectra analysis of the sample resulting after the *Mucoriopsis ellipsoidus* sample is subjected to a lipid extraction treatment and the supernatant is vacuum dried according to the methods detailed in Section 5.3.

Lipid Extraction. The fungal species *Mucoriopsis ellipsoidus* was grown on MEA media, defined above, at 25° C. and the cells harvested. Methanol was then added to the sample and the mixture was incubated at room temperature for 2 hours, with gentle agitation. The sample was then centrifuged at 15400×G for 15 minutes. The pellet and supernatant were vacuum dried. The supernatant and pellet products were characterized by infra-red spectral analyses. See FIGS. 7 and 8, respectively.

Figure 9:
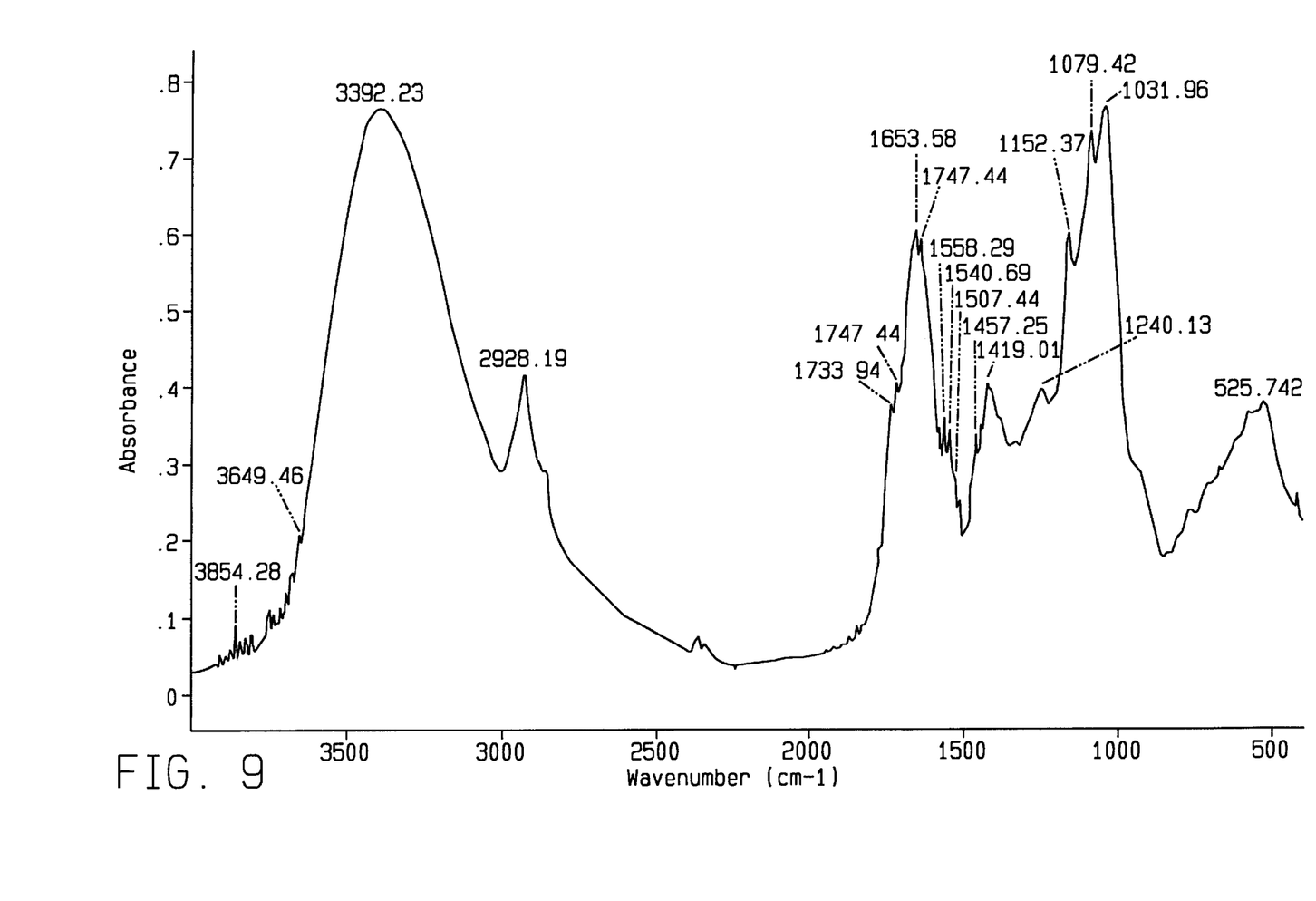
FIG. 9. Infra-red spectra analysis of the sample resulting after the *Mucoriopsis ellipsoidus* sample is subjected to a hot water extraction and the supernatant is vacuum dried according to the methods detailed in Section 5.3.

Hot water treatment. The fungal species *Mucoriopsis ellipsoidus* was grown on MEA media, defined above, at 25° C. and the cells harvested. Water having a temperature of 60° C. was added to the sample and the resulting solution was incubated at 60° C. for 2 hours with gentle agitation and then centrifuged at 15400×G for 15 minutes. The supernatant was vacuum dried. The product was characterized by and infra-red spectral analysis. FIG. 9.

Chitin identification. Identification of chitin was performed using infra-red spectrum analysis according to the KBr pellet method of "Chitin, Chitosan experimental manual" First Edition, 1991, p.60, Gihodo Publishing K.K. One gram of each sample was dissolved in 50 ml deionized water. 2 M HCl was then added to this solution to obtain a final pH of 1.0. After agitating this solution for 30 minutes, an equal volume of acetone was added. The resulting precipitate was then washed and desalted with a solution of 1:20 volume/volume water-acetone. The compound was then washed with acetone and dried at 70° C. for 3 hours. The pellet was mixed with KBr powder and the IR spectrum was then measured.

$^{13}$C-Cross-polarization/magnetic angle spinning nuclear magnetic resonance ("$^{13}$C-CP/MAS NMR") was performed according to the method of "Chitin, chitosan experimental manual" First Edition, page 69–73, 1991, Gihodo Publishing K.K.

6.2 Results

Figure 5:
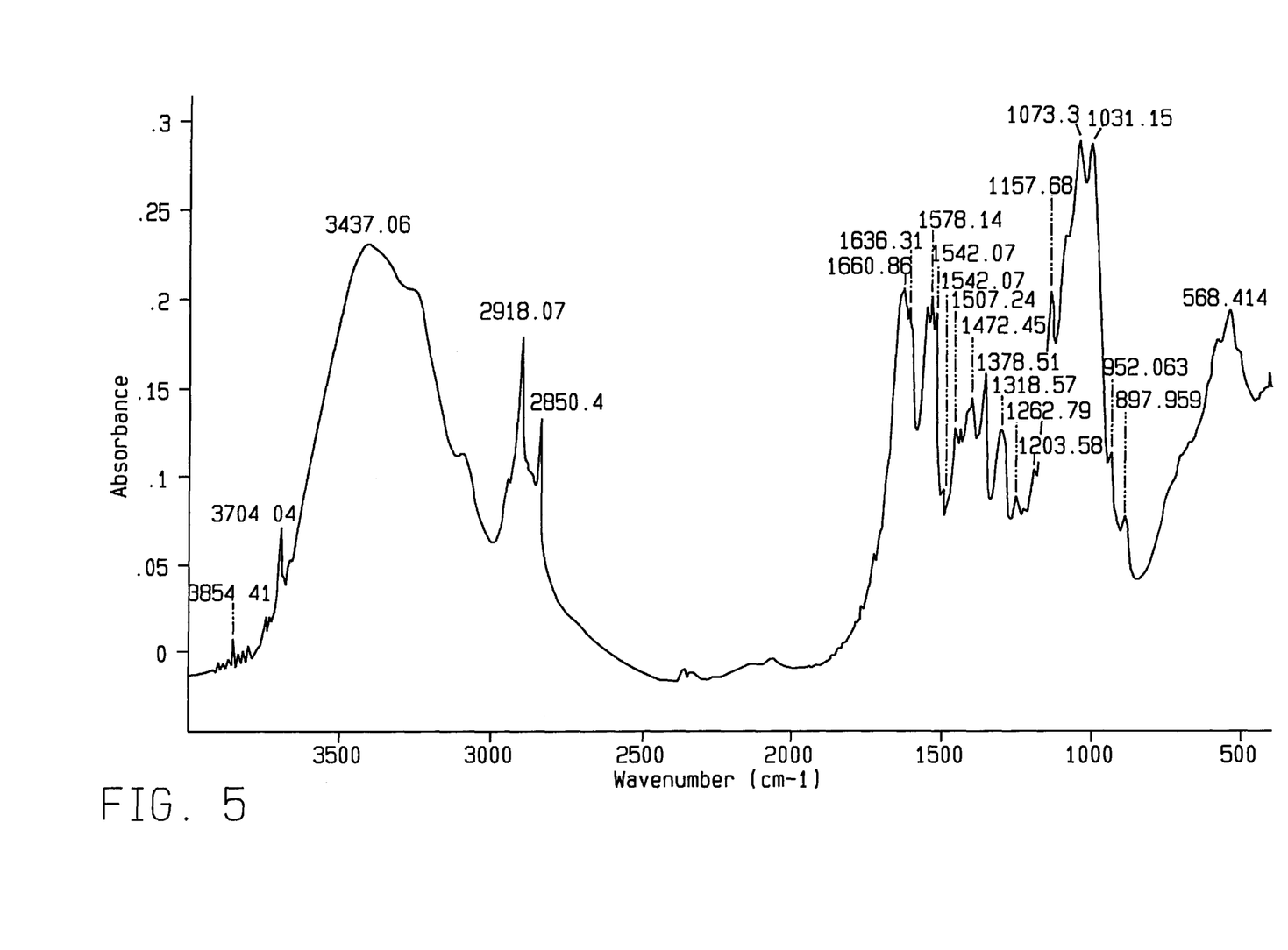
FIG. 5. Infra-red spectra analysis of the sample resulting after the *Mucoriopsis ellipsoidus* alkali treatment precipitate is subjected to a lipid extraction treatment and vacuum dried according to the methods detailed in Section 5.3.
Figure 10A:
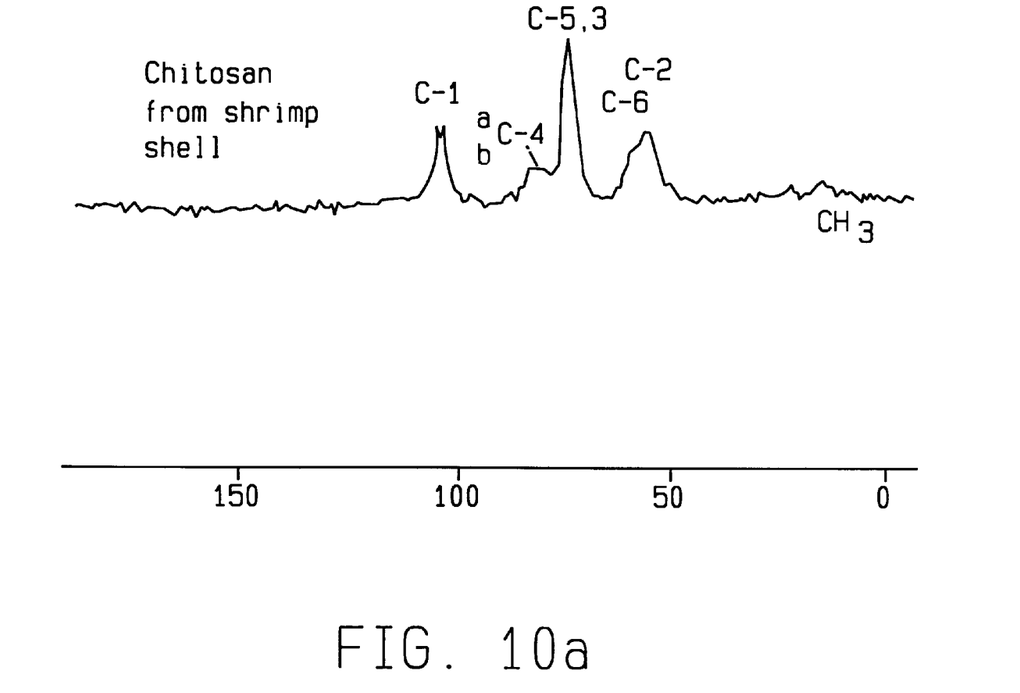
Figure 10B:
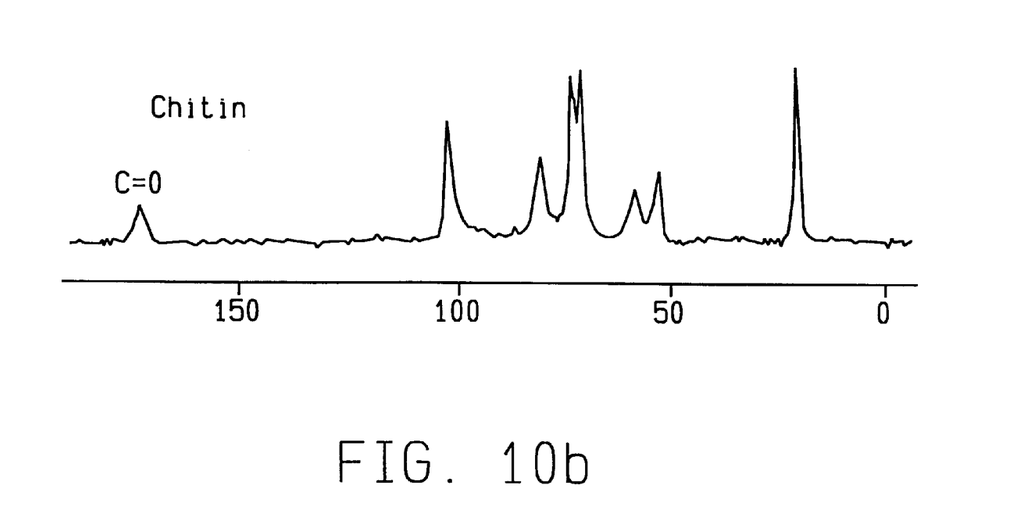
Figure 10C:
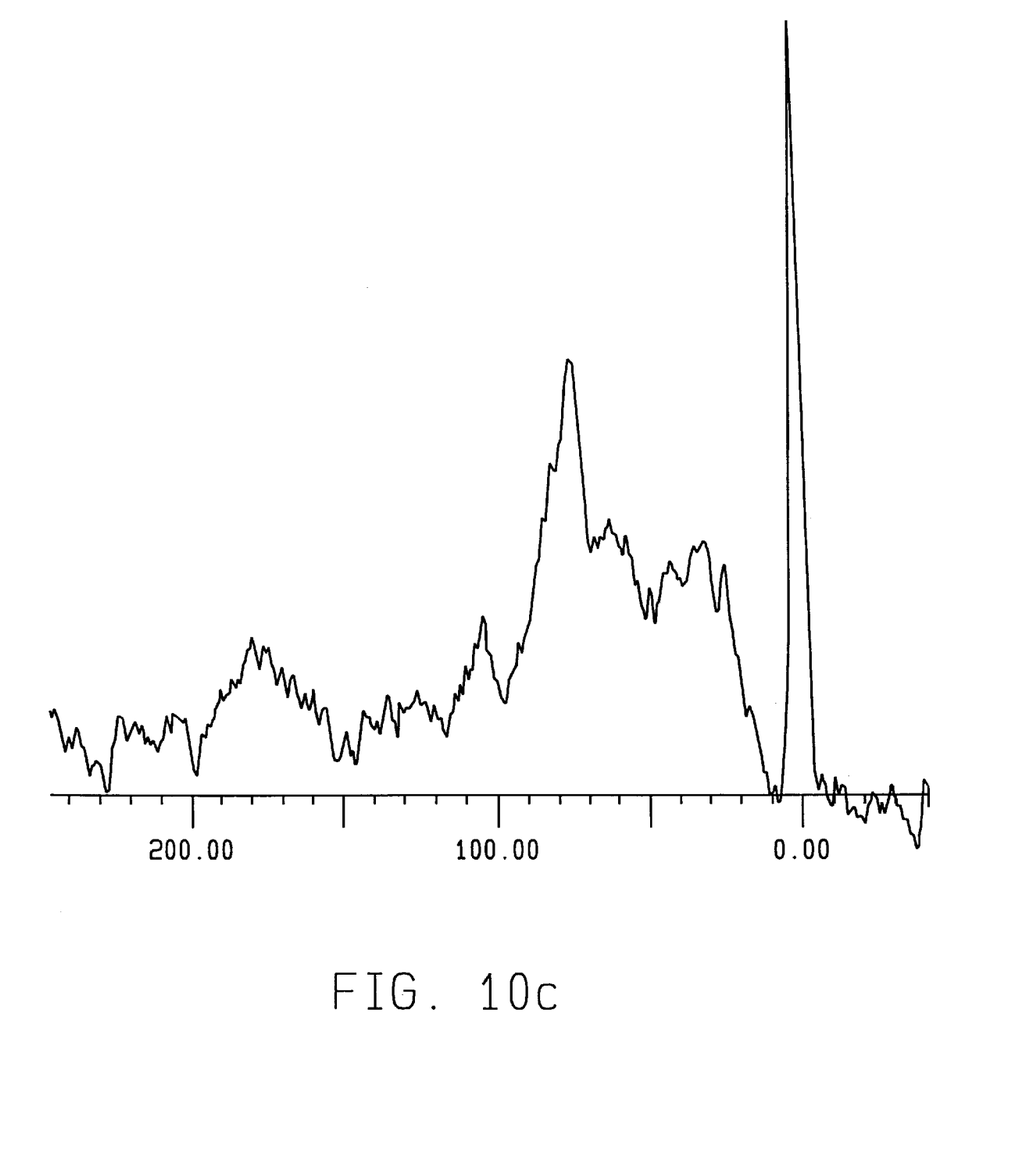

FIGS. 5 and 10 demonstrate that the spectrum of the samples isolated according to the methods of the invention, correspond to those of chitin. Additionally, analysis of the samples suggests that the chitin content of *Mucoriopsis ellipsoidus* was about 6.3% (weight/weight).

Figures 1A, 1B, 1C, 1D:
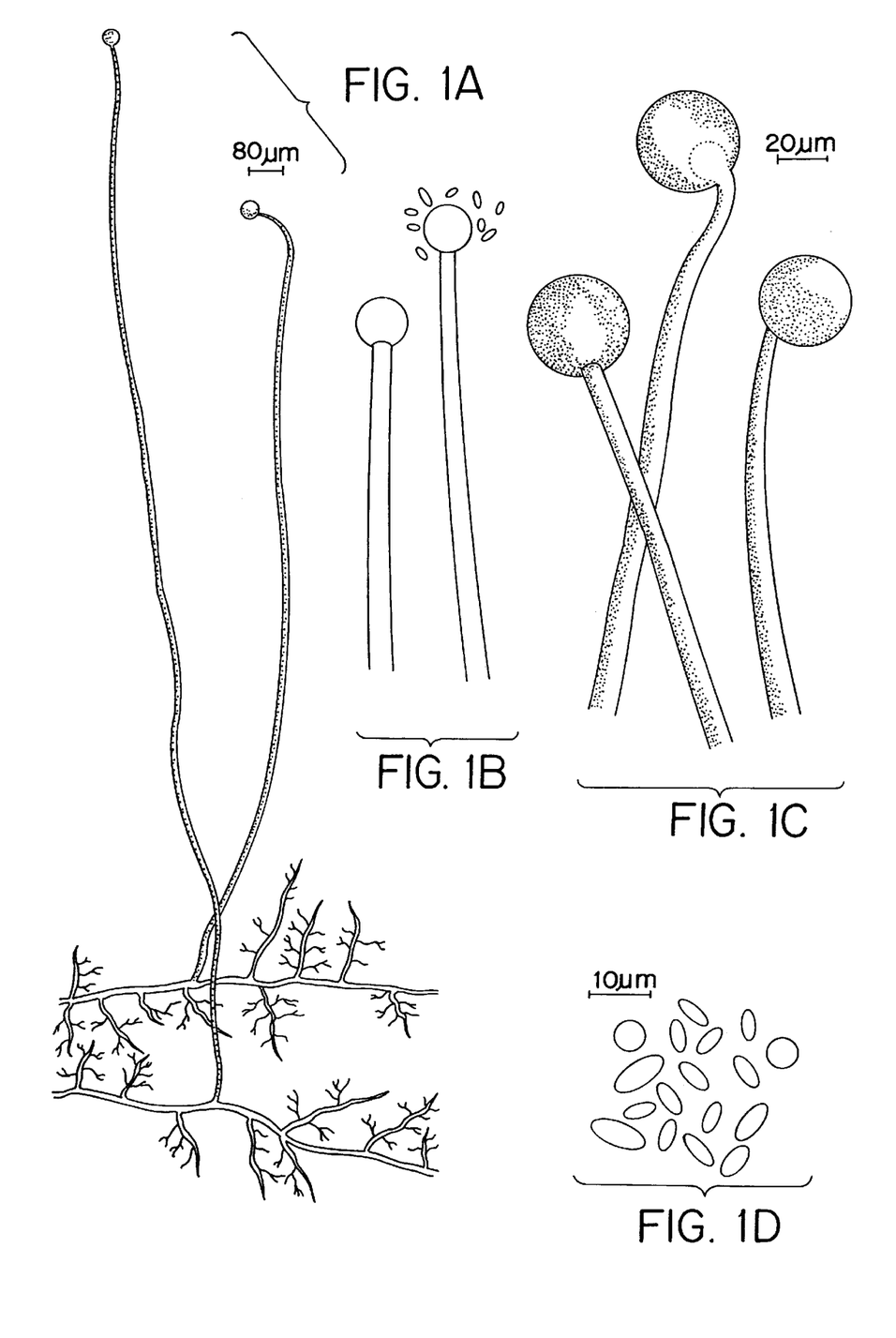
Figure 2:
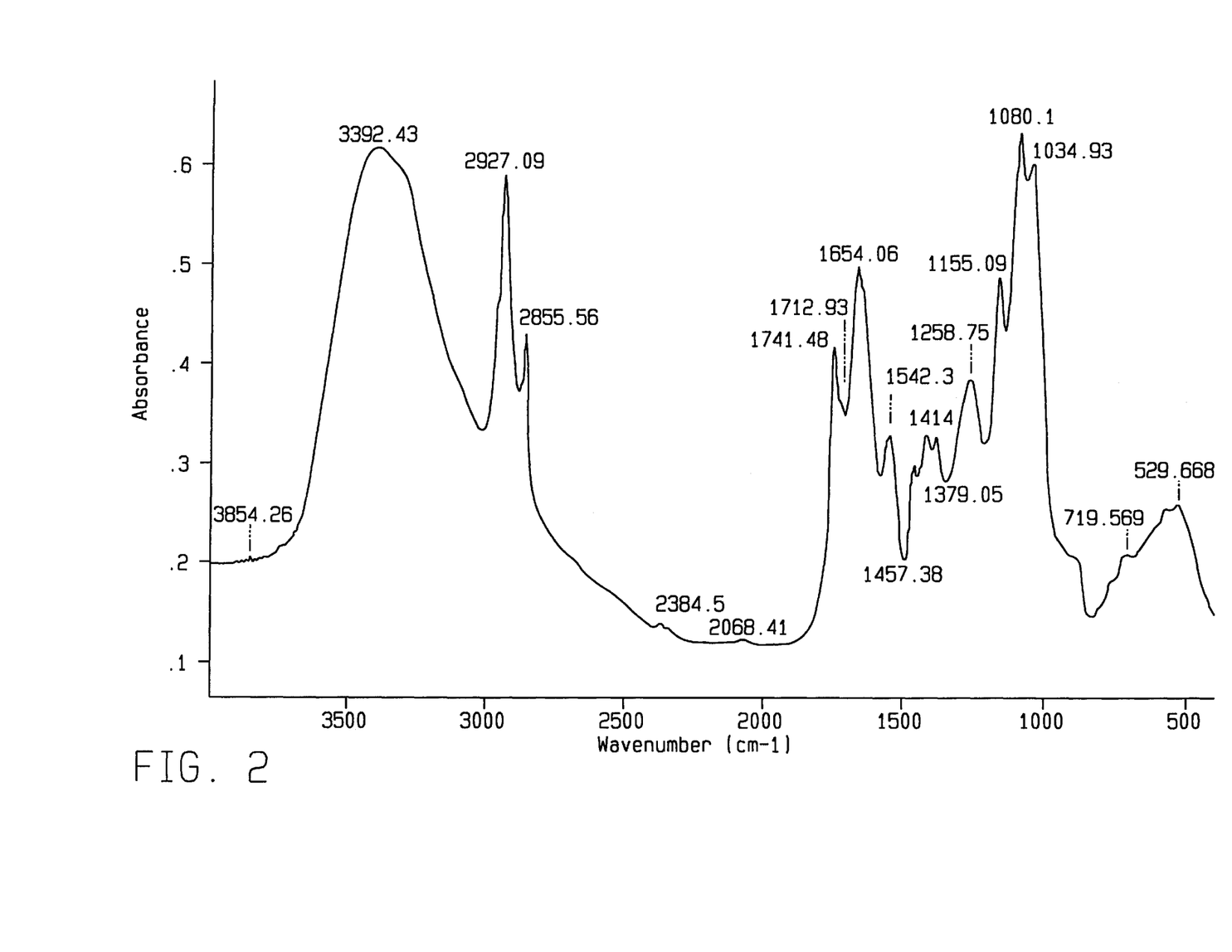
FIG. 2. Infra-red spectra analysis of the crude *Mucoriopsis ellipsoidus* sample (without any extraction).
Figure 3:
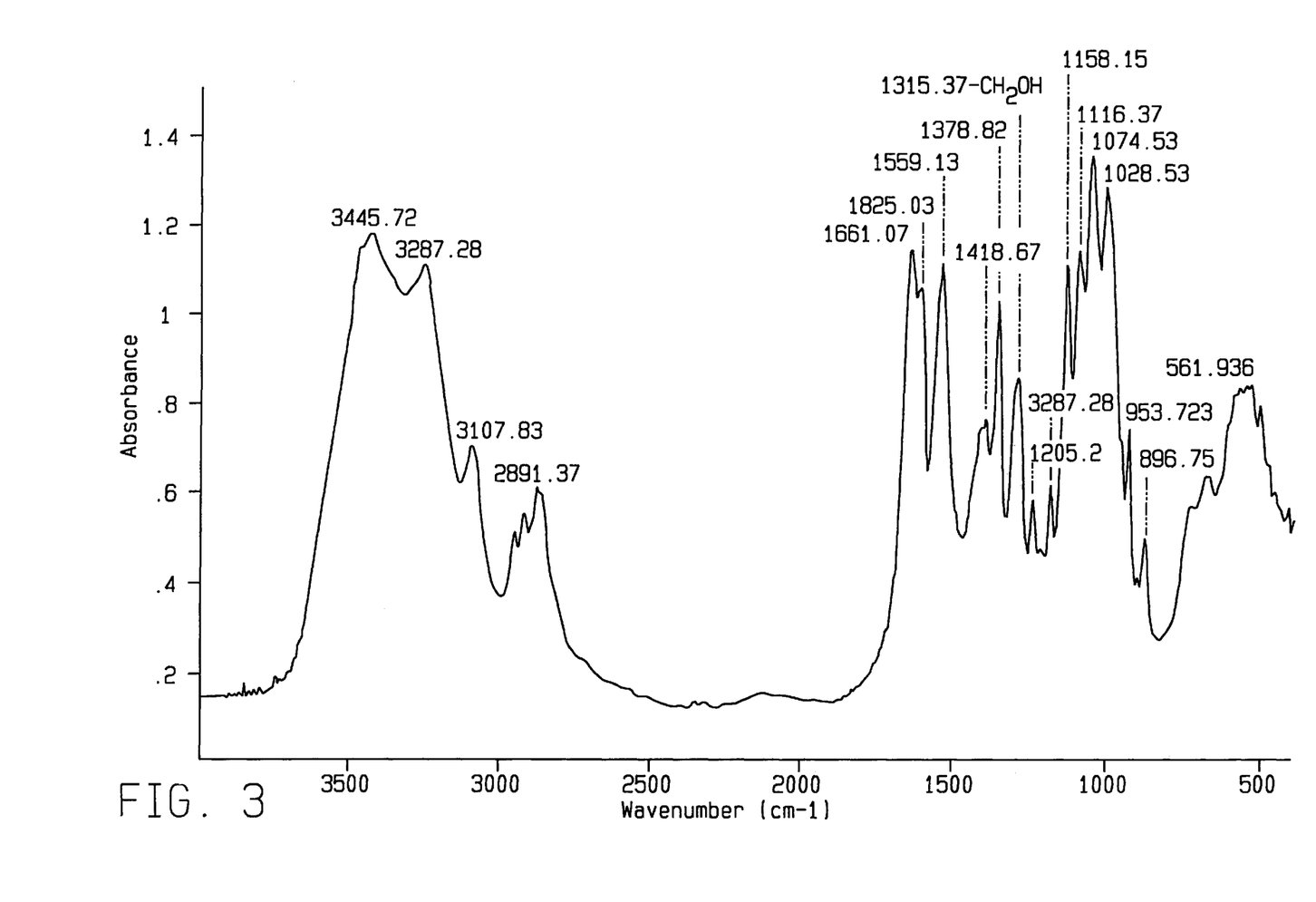
FIG. 3. Infra-red spectra analysis of commercially obtained chitin produced from Queen Crab Shells.
Figure 4:
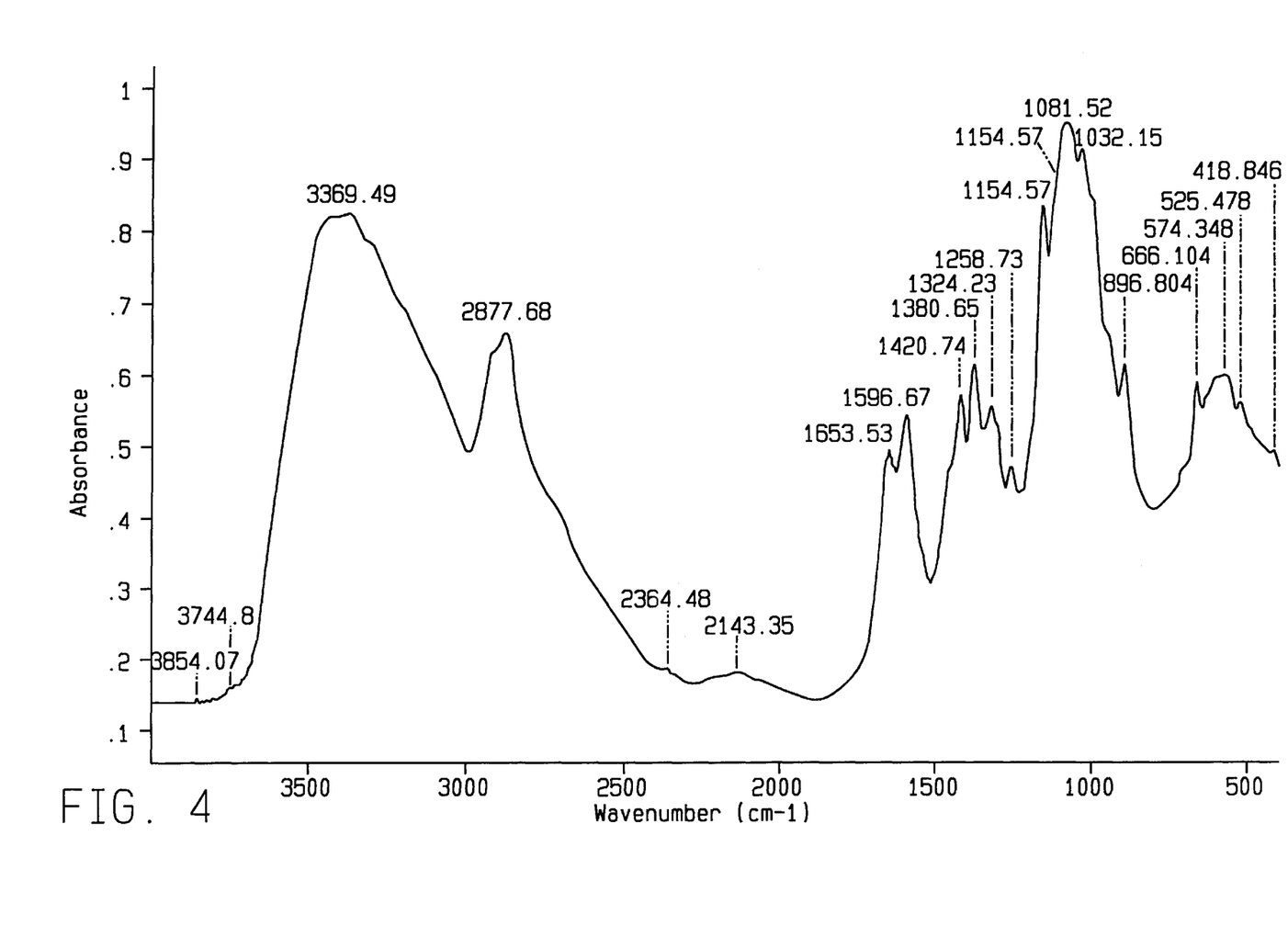
FIG. 4. Infra-red spectra analysis of commercially obtained chitosan produced from Crab Shells.

FIGS. 3 and 4 of the invention represent Infra-red spectra for pure chitin and chitosan, respectively. FIG. 2 represents Infra-red spectra of crude *Mucoriopsis ellipsoidus* sample. Infra-red spectra of the chitin isolated according to the alkali and lipid extraction methods of the invention are shown in FIG. 5. Such physical data corroborates that the compound isolated according to the methods of the invention is chitin. Additionally, NMR analysis of the chitin isolated according to the method of the invention exhibits a pattern substantially similar to that seen for pure chitin. See, FIG. 10. Such an NMR pattern indicates data consistent with the isolated compound from *Mucoriopsis ellipsoidus* being chitin.

It is apparent that many modifications and variations of this invention as set forth herein may be made without departing from the spirit and scope thereof. The specific embodiments described above are given by way of example only, and the invention is limited only by the terms of the appended claims.

7. DEPOSIT OF MUCORIOPSIS *ELLIPSOIDUS*

*Mucoriopsis ellipsoidus* was deposited with the American Type Culture Collection (ATCC), Rockville, Md., on July 16, 1996, and was assigned accession number ATCC 74375.

What is claimed is:

1. A purified, isolated culture of *Mucoriopsis ellipsoidus*, deposited strain ATCC No. 74375, wherein said strain is usable for chitin production.

* * * * *